(12) United States Patent
Cormier et al.

(10) Patent No.: US 7,438,926 B2
(45) Date of Patent: Oct. 21, 2008

(54) METHODS FOR INHIBITING DECREASE IN TRANSDERMAL DRUG FLUX BY INHIBITION OF PATHWAY CLOSURE

(75) Inventors: Michel Cormier, Mountain View, CA (US); Juanita Johnson, Belmont, CA (US); Wei Qi Lin, Palo Alto, CA (US); James Matriano, Mountain View, CA (US); Peter Daddona, Menlo Park, CA (US)

(73) Assignee: Alza Corporation, Mountain View, CA (US)

( * ) Notice: Subject to any disclaimer, the term of this patent is extended or adjusted under 35 U.S.C. 154(b) by 815 days.

(21) Appl. No.: 09/950,436

(22) Filed: Sep. 8, 2001

(65) Prior Publication Data

US 2002/0102292 A1    Aug. 1, 2002

Related U.S. Application Data

(60) Provisional application No. 60/231,160, filed on Sep. 8, 2000.

(51) Int. Cl.
*A61F 13/00* (2006.01)

(52) U.S. Cl. ........................... 424/449; 514/947

(58) Field of Classification Search .............. 435/4, 435/975, 283.1; 424/449; 514/947
See application file for complete search history.

(56) References Cited

U.S. PATENT DOCUMENTS

| | | | |
|---|---|---|---|
| RE25,637 E | 9/1964 | Kravitz et al. ............... 128/253 |
| 3,814,097 A | 6/1974 | Ganderton et al. .......... 128/268 |
| 3,964,482 A | 6/1976 | Gerstel et al. ............... 128/260 |
| 5,250,023 A | 10/1993 | Lee et al. ..................... 604/20 |
| 5,279,544 A | 1/1994 | Gross et al. .................. 604/20 |
| 5,722,397 A | 3/1998 | Eppstein ..................... 128/633 |
| 5,879,326 A | 3/1999 | Godshall et al. ............. 604/51 |
| 5,885,211 A | 3/1999 | Eppstein et al. ............. 600/309 |
| 5,902,603 A * | 5/1999 | Chen et al. ................... 424/449 |
| 6,022,316 A | 2/2000 | Eppstein ..................... 600/309 |
| 6,050,988 A * | 4/2000 | Zuck ........................... 604/890.1 |
| 6,083,196 A * | 7/2000 | Trautman et al. ............ 604/46 |
| 6,230,051 B1 | 5/2001 | Cormier et al. |
| 6,322,808 B1 | 11/2001 | Trautman et al. |
| 6,918,901 B1 | 7/2005 | Theeuwes et al. |
| 6,953,589 B1 | 10/2005 | Trautman et al. |
| 7,184,826 B2 | 2/2007 | Cormier et al. |
| 2002/0032415 A1* | 3/2002 | Trautman et al. ............ 604/272 |
| 2002/0102292 A1* | 8/2002 | Cormier et al. ............. 424/449 |
| 2002/0128599 A1 | 9/2002 | Cormier et al. |
| 2004/0115167 A1* | 6/2004 | Cormier et al. ............. 424/85.1 |
| 2006/0200069 A1* | 9/2006 | Cormier et al. ............. 604/46 |

FOREIGN PATENT DOCUMENTS

| | | |
|---|---|---|
| WO | WO 96/17648 | 6/1996 |
| WO | WO 96/37155 | 11/1996 |
| WO | WO 96/37256 | 11/1996 |
| WO | WO 97/03718 | 2/1997 |
| WO | WO 97/48440 | 12/1997 |
| WO | WO 97/48441 | 12/1997 |
| WO | WO 97/48442 | 12/1997 |
| WO | WO 98/00193 | 1/1998 |
| WO | WO 98/11937 | 3/1998 |
| WO | WO 98/28037 | 7/1998 |
| WO | WO 98/29134 * | 7/1998 |
| WO | WO 98/29365 | 7/1998 |
| WO | WO 99/29298 | 6/1999 |
| WO | WO 99/64580 | 12/1999 |
| WO | WO 2000/74763 A2 | 12/2000 |
| WO | WO 2001/41864 A1 | 6/2001 |
| WO | WO 2000/74763 A3 | 7/2001 |

OTHER PUBLICATIONS

Academician of Rams V.I. Pokrovsky, Moscow, Meditsina; Medical leech; Small Medical Encyclopedia; 4; p. 373; 1996 (in Russian with English translation).

ADAD. G.I. Nikonov, Hirudotherapy and Hyrudopharmacotherapy. p. 82-83; 1996. (in Russian with English translation).

* cited by examiner

*Primary Examiner*—Ralph Gitomer
(74) *Attorney, Agent, or Firm*—Edwards Angell Palmer & Dodge LLP; Kathleen Williams; Jeffrey L. Kopacz

(57) ABSTRACT

This invention relates to a method for inhibiting a decrease in the transdermal flux of an agent that is being transdermally delivered or sampled over a prolonged period of time wherein the delivery or sampling involves disrupting at least the stratum corneum layer of the skin to form pathways through which the agent passes. The desired result is achieved by co-delivering or co-sampling the agent with an amount of at least one anti-healing agent wherein the amount of the anti-healing agent is effective in inhibiting a decrease in the agent transdermal flux compared to when the delivery or sampling of the agent is done under substantially identical conditions except in the absence of the anti-healing agent(s).

24 Claims, 8 Drawing Sheets

METHODS FOR INHIBITING DECREASE IN TRANSDERMAL DRUG FLUX BY INHIBITION OF PATHWAY CLOSURE

This application claims benefit of provisional application Ser. No. 60/231,160 filed Sep. 8, 2000.

TECHNICAL FIELD

This invention relates to inhibiting a decrease in the transdermal flux of an agent by inhibiting pathway closure. In particular this invention relates to a method for inhibiting a decrease in the transdermal flux of an agent that is being transdermally delivered or sampled over a prolonged period of time wherein the delivery or sampling involves disrupting at least the stratum corneum layer of the skin to form pathways through which the agent passes by co-delivering or co-sampling the agent with an amount of at least one anti-healing agent wherein the amount of the anti-healing agent is effective in inhibiting a decrease in the agent transdermal flux compared to when the delivery or sampling of the agent is done under substantially identical conditions except in the absence of the anti-healing agent(s).

BACKGROUND ART

Drugs are most conventionally administered either orally or by injection. Unfortunately, many medicaments are completely ineffective or of radically reduced efficacy when orally administered since they either are not absorbed or are adversely affected before entering the blood stream and thus do not possess the desired activity. On the other hand, the direct injection of the medicament into the blood stream, while assuring no modification of the medicament in administration, is a difficult, inconvenient and uncomfortable procedure, sometimes resulting in poor patient compliance. Transdermal drug delivery offers improvements in these areas. However, in many instances, the rate of delivery or flux of many agents via the passive transdermal flux is too limited to be therapeutically effective.

One method of increasing the transdermal flux of agents relies on the application of an electric current across the body surface referred to as "electrotransport." "Electrotransport" refers generally to the passage of a beneficial agent, e.g., a drug or drug precursor, through a body surface, such as skin, mucous membranes, nails, and the like where the agent is induced or enhanced by the application of an electrical potential. The electrotransport of agents through a body surface may be attained in various manners. One widely used electrotransport process, iontophoresis, involves the electrically induced transport of charged ions. Electroosmosis, another type of electrotransport process, involves the movement of a solvent with the agent through a membrane under the influence of an electric field. Electroporation, still another type of electrotransport, involves the passage of an agent through pores formed by applying a high voltage electrical pulse(s) to a membrane. In many instances, more than one of these processes may be occurring simultaneously to a different extent. Accordingly, the term "electrotransport" is given herein its broadest possible interpretation, to include the electrically induced or enhanced transport of at least one charged or uncharged agent, or mixtures thereof, regardless of the specific mechanism or mechanisms by which the agent is actually being transported. Electrotransport delivery generally increases agent flux during transdermal delivery.

Another method of increasing the agent flux involves pretreating the skin with, or co-delivering with the beneficial agent, a skin permeation enhancer. A permeation enhancer substance, when applied to a body surface through which the agent is delivered, enhances its flux therethrough such as by increasing the permselectivity and/or permeability of the body surface, creating hydrophilic pathways through the body surface, and/or reducing the degradation of the agent during transport. This methodology is typically used when the drug is delivered transdermally by passive diffusion.

There also have been many attempts to mechanically penetrate or disrupt the skin thereby creating pathways into the skin in order to enhance the transdermal flux. Some of the earliest attempts to enhance transdermal drug flux involved abrading the skin (e.g., with sandpaper) or tape-stripping the skin to disrupt the stratum corneum. More recently, there have been attempts to pierce or cut through the stratum corneum with tiny piercing/cutting elements. See for example, U.S. Pat. Nos. 5,879,326 issued to Godshall, et al., 3,814,097 issued to Ganderton, et al., 5,279,544 issued to Gross, et al., 5,250,023 issued to Lee, et al., 3,964,482 issued to Gerstel, et al., Reissue 25,637 issued to Kravitz, et al., and PCT Publication Nos. WO 96/37155, WO 96/37256, WO 96/17648, WO 97/03718, WO 98/11937, WO 98/00193, WO 97/48440, WO 97/48441, WO 97/48442, WO 98/00193, WO 99/64580, WO 98/28037, WO 98/29298 and WO 98/29365. These devices use piercing elements of various shapes and sizes to pierce the outermost layer (i.e., the stratum corneum) of the skin. The piercing elements disclosed in these references generally extend perpendicularly from a thin, flat member, such as a pad or sheet. The piercing elements or microprotrusion in some of these devices are extremely small, some having dimensions (i.e., length and width) of only about 25-400 μm and a microprotrusion thickness of only about 5-50 μm. These tiny piercing/cutting elements make correspondingly small microslits/microcuts in the stratum corneum for enhanced transdermal agent delivery therethrough.

It has now been discovered that in the case of human skin, the pathways created by the microslits/microcuts are quickly closed and sealed by the skin's natural healing processes. Although this process is not completely understood at this time, it is believed that it is closely related to wound healing. Wound healing is a complex phenomenon involving many biological processes. The earliest event, taking place within minutes, in the wound healing process is the formation of a fibrin clot. In addition, many pro-inflammation mediators are liberated or generated during the early phase of wound healing. Liberation of these factors triggers keratinocyte migration, leukocyte infiltration, fibroblast proliferation which result in protein degradation, protein synthesis and tissue remodeling. In the end, reformation of the skin barrier is achieved. In some instances, the enhancement in transdermal agent flux provided by these pathways is completely eliminated within several hours of making the pathways. Thus, there is a need for a method which can prevent, or at least delay the skin's natural healing processes in order to allow transdermal flux of agents, through microcuts/microslits over longer periods of time (e.g., longer than about one hour) when the delivery methodology utilizes micropiercing elements.

The present invention fulfills this and related needs.

DISCLOSURE OF THE INVENTION

This invention is directed to a method for inhibiting a decrease in the transdermal flux of an agent which is being transdermally delivered or sampled over a prolonged period of time where the transdermal flux involves disrupting at least the stratum corneum layer of the skin. Specifically, it has been discovered that by co-delivering or co-sampling the agent in the presence of an anti-healing agent the closure of the pathways in the skin formed as a result of disrupting the stratum corneum layer of the skin can be inhibited, thereby inhibiting a decrease in the transdermal flux of the agent.

Accordingly, in a first aspect, this invention is directed to a method for inhibiting a decrease in the transdermal flux of an agent being transdermally delivered or sampled over a prolonged period of time wherein the delivery involves disrupting (e.g., by puncturing) at least the stratum corneum layer of the skin to form a plurality of pathways through which the agent passes which method comprises co-delivering or co-sampling the agent with an amount of at least one anti-healing agent wherein said amount of said anti-healing agent is effective in inhibiting a decrease in said agent transdermal flux compared to delivering or sampling said agent under substantially identical conditions except in the absence of said anti-healing agent(s).

In a second aspect, this invention is directed to a method for transdermally delivering an agent over a prolonged period of time which method comprises:
(i) forming a plurality of micro-disruptions through the stratum corneum layer of the skin to form pathways through which the agent passes; and
(ii) placing a reservoir in agent transmitting relation with the micro-disruptions formed in step (i) said reservoir comprising the agent and an amount of at least one anti-healing agent wherein said amount of said anti-healing agent is effective in inhibiting the decrease in said agent transdermal flux compared to delivering said agent under substantially identical conditions except in the absence of said anti-healing agent(s).

In a third aspect, this invention is directed to a method for transdermally sampling an agent over a prolonged period of time which method comprises:
(i) forming a plurality of micro-disruptions through the stratum corneum layer of the skin to form pathways through which the agent passes; and
(ii) placing a reservoir in agent transmitting relation with the micro-disruptions formed in step (i) said reservoir comprising an amount of at least one anti-healing agent wherein said amount of said anti-healing agent is effective in inhibiting the decrease in said agent transdermal flux compared to sampling said agent under substantially identical conditions except in the absence of said anti-healing agent(s).

In the above methods, at least the stratum corneum layer of the skin is pierced, cut or otherwise disrupted (e.g., by abrasives or tape stripping) and most preferably at least the stratum corneum layer of the skin is perforated with a skin perforating device having a plurality of microprotrusions which can penetrate the stratum corneum of the skin to form a plurality of pathways through which the agent and the anti-healing agent pass. The anti-healing agent(s) is delivered either before the agent is delivered or sampled; or before and during the transdermal flux of the agent; or during the transdermal flux of the agent; or during and after the transdermal flux of the agent.

In the above methods, preferably, the anti-healing agent(s) is selected from the group consisting of anticoagulants, anti-inflammatory agents, agents that inhibit cellular migration, and osmotic agents in an amount effective to generate, in solution, an osmotic pressure greater than about 2000 kilopascals, preferably greater than about 3000 kilopascals at 20° C. or mixtures thereof.

Preferably, the anticoagulant is selected from the group consisting of heparin having a molecular weight from 3000 to 12,000 daltons, pentosan polysulfate, citric acid, citrate salts, EDTA, and dextrans having a molecular weight from 2000 to 10,000 daltons.

Preferably the anti-inflammatory agent is selected from the group consisting of hydrocortisone sodium phosphate, betamethasone sodium phosphate, and triamcinolone sodium phosphate.

Preferably, the agent that inhibits the cellular migration is selected from the group consisting of laminin and related peptides.

Preferably, the osmotic agent is a biologically compatible salt such as sodium chloride or a neutral compound such as glucose, or a zwitterionic compound such as glycine having a sufficiently high concentration to generate, in solution, an osmotic pressure greater than about 2000 kilopascals, preferably greater than about 3000 kilopascals.

Preferably, the agent that is transdermally delivered is a macromolecular agent selected from the group consisting of polypeptides, proteins, oligonucleotides, nucleic acids, and polysaccharides.

Preferably, the polypeptides and proteins are selected from the group selected from desmopressin, leutinizing releasing hormone (LHRH) and LHRH analogs (e.g., goserelin, leuprolide, buserelin, triptorelin), PTH, calcitonin, interferon-$\alpha$, interferon-$\beta$, interferon-$\gamma$, follicle stimulating hormone (FSH), hGH, insulin, insulinotropin, and erythropoietin.

Preferably, the oligonucleotide is selected from the group consisting of ISIS 2302, ISIS 15839 and other phosphorothiolated oligonucleotides and other methoxyethylphosphorothiolated oligonucleotides and the polysaccharide is selected from the group consisting of low molecular weight heparin having a molecular weight from 3000 to 12,000 daltons and pentosan polysulfate.

Preferably, the agent that is transdermally sampled is a body analyte. Preferably, the body analyte is glucose.

Preferably, the agent and the anti-healing agent(s) are delivered transdermally by passive diffusion and/or electrotransport.

In a fourth aspect, this invention is directed to a device for transdermally delivering an agent over a prolonged period of time which device comprises:
(i) an element having a plurality of skin-piercing microprotrusions for forming a plurality of microcuts through the stratum corneum layer of the skin to form pathways through which the agent passes; and
(ii) a reservoir comprising an agent and an amount of at least one anti-healing agent wherein said amount of said anti-healing agent is effective in inhibiting the decrease in said agent transdermal flux compared to delivering said agent under substantially identical conditions except in the absence of said anti-healing agent(s).

In a fifth aspect, this invention is directed to a device for transdermally sampling an agent over a prolonged period of time, which device comprises:
(i) an element having a plurality of skin piercing microprotrusions for forming a plurality of microcuts through the stratum corneum layer of the skin to form pathways through which the agent passes; and
(ii) a reservoir comprising an amount of at least one anti-healing agent wherein said amount of said anti-healing agent is effective in inhibiting a decrease in agent transdermal flux compared to sampling the agent under substantially identical conditions except in the absence of said anti-healing agent(s).

In a sixth aspect, this invention is directed to a kit transdermally delivering or sampling an agent over a prolonged period of time comprising:

(i) a device with an array of microprotrusions for forming microcuts through the stratum corneum layer of the skin; and (ii) a reservoir comprising an amount of at least one anti-healing agent wherein said amount of said anti-healing agent is effective in inhibiting a decrease in an agent transdermal flux compared to when the agent is delivered or sampled under substantially identical conditions except in the absence of said anti-healing agent.

Preferably, the anti-healing agent(s) is selected from the group consisting of anticoagulants, anti-inflammatory agents, agents that inhibit cellular migration, and osmotic agents in an amount effective to generate, in solution, an osmotic pressure greater than about 2000 kilopascals, preferably greater than about 3000 kilopascals at 20° C. or mixtures thereof.

Preferably, the anticoagulant is selected from the group consisting of heparin having a molecular weight from 3000 to 12,000 daltons, pentosan polysulfate, citric acid, citrate salts such as sodium citrate, EDTA, and dextrans having molecular weight from 2000 to 10,000 daltons.

Preferably the anti-inflammatory agent is selected from the group consisting of hydrocortisone sodium phosphate, betamethasone sodium phosphate, and triamcinolone sodium phosphate.

Preferably, the agent that inhibits the cellular migration is selected from the group consisting of laminin and related peptides.

Preferably, the osmotic agent is a biologically compatible salt such as sodium chloride or a neutral compound such as glucose, or a zwitterionic compound such as glycine having a sufficiently high concentration to generate, in solution, an osmotic pressure greater than about 2000 kilopascals, preferably greater than about 3000 kilopascals.

Preferably, the agent that is transdermally delivered is a macromolecular agent selected from the group consisting of polypeptides, proteins, oligonucleotides, nucleic acids, and polysaccharides.

Preferably, the polypeptides and proteins are selected from the group selected from desmopressin, leutinizing releasing hormone (LHRH) and LHRH analogs (e.g., goserelin, leuprolide, buserelin, triptorelin), PTH, calcitonin, interferon-$\alpha$, interferon-$\beta$, interferon-$\gamma$, follicle stimulating hormone (FSH), hGH, insulin, insulinotropin, and erythropoietin.

Preferably, the oligonucleotide is selected from the group consisting of ISIS 2302, ISIS 15839 and other phosphorothiolated oligonucleotides and other methoxyethylphosphorothiolated oligonucleotides and the polysaccharide is selected from the group consisting of low molecular weight heparin having a molecular weight from 3000 to 12,000 daltons and pentosan polysulfate.

Preferably, the agent that is transdermally sampled is a body analyte. Preferably, the body analyte is glucose.

BRIEF DESCRIPTION OF THE DRAWINGS

The invention will now be described in greater detail with reference to the accompanying drawings, wherein.

DETAILED DESCRIPTION OF THE INVENTION

Figure 1:
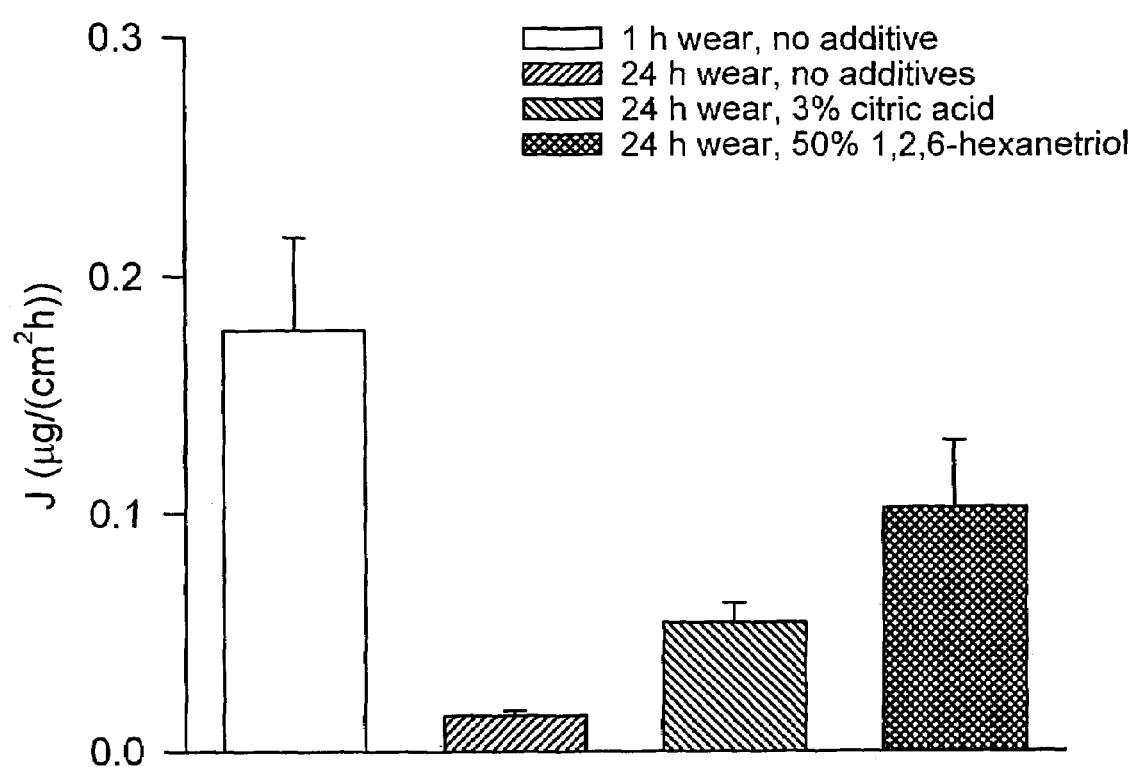
FIG. 1 is a graph of the effect of pathway closure inhibitors on passive transdermal pentosan polysulfate flux.

Definitions:
Unless stated otherwise the following terms used in this application have the following meanings.

The term "transdermal flux" means the rate of passage of any agent in and through the skin of an individual or the rate of passage of any analyte out through the skin of an individual.

The term "transdermal" means the delivery or extraction of an agent through the skin.

The term "pathway" means passages formed in the stratum corneum of the skin by disrupting it which allow for enhanced transdemal flux of an agent. The stratum corneum of the skin can be disrupted by methods well known in the art such as sanding, tape stripping, creating microcuts, and the like. Other methods are described in U.S. Pat. Nos. 6,022,316, 5,885,211 and 5,722,397 the disclosures of which are incorporated herein in their entirety. Preferably the passages are formed by disrupting of the skin with a device having a plurality of stratum corneum-piercing microprotrusions thereby creating microcuts in the stratum corneum The term "microprotrusion" as used herein refers to very tiny stratum corneum piercing elements typically having a length of less than 500 micrometers, and preferably less than 250 micrometer, which make a penetration in the stratum corneum. In order to penetrate the stratum corneum, the microprotrusions preferably have a length of at least 50 micrometers. The microprotrusions may be formed in different shapes, such as needles, hollow needles, blades, pins, punches, and combinations thereof.

The term "microprotrusion array" as used herein refers to a plurality of microprotrusions arranged in an array for piercing the stratum corneum. The microprotrusion array may be formed by etching a plurality of blades from a thin sheet and folding each of the blades out of the plane of the sheet to form the configuration shown in FIG. 8. The microprotrusion array may also be formed in other known manners, such as by connecting multiple strips having microprotrusions along an edge of each of the strips. The microprotrusion array may include hollow needles which inject a liquid formulation. Examples of microprotrusion arrays are described in U.S. Pat. No. 5,879,326 issued to Godshall, et al., 3,814,097 issued to Ganderton, et al., 5,279,544 issued to Gross, et al., 5,250,023 issued to Lee, et al., 3,964,482 issued to Gerstel, et al., Reissue 25,637 issued to Kravitz, et al., and PCT Publication Nos. WO 96/37155, WO 96/37256, WO 96/17648, WO 97/03718, WO 98/11937, WO 98/00193, WO 97/48440, WO 97/48441, WO 97/48442, WO 98/00193, WO 99/64580, WO 98/28037, WO 98/29298, and WO 98/29365, all of which are incorporated herein by reference in their entirety.

The term "prolonged delivery" as used herein means a period of delivery that lasts for at least half an hour, preferably between several hours to about 24 hours, more preferably between about 8 and 24 hours.

The term "co-delivering" as used herein means the anti-healing agent(s) is administered transdermally before the agent is delivered; before and during transdermal flux of the agent; during transdermal flux of the agent; and/or during and after transdermal flux of the agent.

The term "co-sampling" as used herein means the antihealing agent(s) is administered transdermally before the agent is sampled by transdermal flux; before and during transdermal flux of the agent; during transdermal flux of the agent; and/or during and after transdermal flux of the agent.

For the purposes for transdermal delivery, the term "agent" as used herein refers to an agent, drug, compound, composition of matter or mixture thereof which provides some pharmacological, often beneficial, effect. It is intended in its broadest interpretation as any pharmaceutically-acceptable substance which may be delivered to a living organism to produce a desired, usually beneficial, effect. In general, this includes therapeutic agents in all of the major therapeutic fields including, but not limited to, anti-infectives such as antibiotics and antiviral agents; analgesics such as fentanyl, sufentanil, and buprenorphine, and analgesic combinations; anesthetics; anorexics; antiarthritics; antiasthmatic agents such as terbutaline; anticonvulsants; antidepressants; antidiabetics agents; antidiarrheals; antihistamines; antiinflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics including gastrointestinal and urinary; anticholinergics; sympathomimetrics; xanthine derivatives; cardiovascular preparations including calcium channel blockers such as nifedipine; betaagonists such as dobutamine and ritodrine; beta blockers; antiarrythmics; antihypertensives such as atenolol; ACE inhibitors such as ranitidine; diuretics; vasodilators including general, coronary, peripheral and cerebral; central nervous systems stimulants; cough and cold preparations; decongestants; diagnostics; hormones such as parathyroid hormones; hypnotics; immunosuppressives; muscle relaxants; parasympatholytics; parasympathomimetrics; prostaglandins; proteins; peptides; psychostimulants; vaccines, sedatives and tranquilizers.

The invention is particularly useful in the controlled delivery of peptides, polypeptides, proteins, or other macromolecules difficult to deliver transdermally because of their size. These macromolecular substances typically have a molecular weight of at least about 300 Daltons, and more typically, in the range of about 300 to 40,000 Daltons. Examples of polypeptides and proteins which may be delivered in accordance with the present invention include, without limitation, LHRH, LHRH analogs (such as goserelin, leuprolide, buserelin, triptorelin, gonadorelin, napharelin and leuprolide), GHRH, GHRF, insulin, insulinotropin, calcitonin, octreotide, endorphin, TRH, NT-36 (chemical name: N-[[(s)-4-oxo-2-azetidinyl]-carbonyl]-L-histidyl-L-prolinamide), liprecin, pituitary hormones (eg, HGH, HMG, HCG, desmopressin acetate, etc), follicle luteoids, $\alpha$-ANF, growth factor such as releasing factor (GFRF), $\beta$-MSH, GH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirudin and hirudin analogs such as hirulog, hyaluronidase, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSI's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, PTH, heparin having a molecular weight from 3000 to 12,000 daltons, vaccines, vasopressin antagonist analogs, interferon-$\alpha$, -$\beta$, and -$\gamma$, alpha-1 antitrypsin (recombinant), and TGF-beta.

It is to be understood that more than one agent may be incorporated into the agent formulation in the method of this invention, and that the use of the term "agent" in no way excludes the use of two or more such agents or drugs.

The agents can be in various forms, such as free bases, acids, charged or uncharged molecules, components of molecular complexes or nonirritating, pharmacologically acceptable salts. Also, simple derivatives of the agents (such as ethers, esters, amides, etc) which are easily hydrolyzed by body pH, enzymes, etc, can be employed. The agents can be in solution, in suspension or a combination of both in the drug reservoir. Alternatively, the agent can be a particulate.

The amount of agent employed in the delivery device will be that amount necessary to deliver a therapeutically effective amount of the agent to achieve the desired result. In practice, this will vary widely depending upon the particular agent, the site of delivery, the severity of the condition, and the desired therapeutic effect. Thus, it is not practical to define a particular range for the therapeutically effective amount of agent incorporated into the method.

For the purposes for transdermal sampling, the term "agent" as used herein refers to body analytes to be sampled. The term "analyte" as used herein means any chemical or biological material or compound suitable for passage through a biological membrane by the technology taught in this present invention, or by technology previously known in the art, of which an individual might want to know the concentration or activity inside the body. Glucose is a specific example of an analyte because it is a sugar suitable for passage through the skin, and individuals, for example those having diabetes, might want to know their blood glucose levels. Other examples of analytes include, but are not limited to, such compounds as sodium, potassium, bilirubin, urea, ammonia, calcium, lead, iron, lithium, salicylates, alcohol, licit substances, illicit drugs, and the like.

The term "therapeutic" amount or rate refer to the amount or rate of the agent needed to effect the desired pharmacological, often beneficial, result.

The term "passive" transdermal delivery, is used herein to describe the passage of an agent through a body surface, eg, skin by passive diffusion. Typically, passive delivery devices have a drug reservoir which contains a high concentration of a drug. The device is placed in contact with a body surface for an extended period of time, and is allowed to diffuse from the reservoir and into the body of the patient, which has a much lower concentration of drug. The primary driving force for passive drug delivery is the concentration gradient of the drug across the skin. In this type of delivery, the drug reaches the bloodstream by diffusion through the dermal layers of the body. The preferred agents for passive delivery are hydrophobic non-ionic agents, given that the drug must diffuse through the lipid layers of the skin.

The term "electrotransport" is used herein to describe the passage of a substance, eg, a drug or prodrug, through a body surface or membrane, such as the skin, mucous membranes, or nails, induced at least partially by the application of an electric field across the body surface (eg, skin). A widely used electrotransport process, iontophoresis, involves the electrically induced transport of therapeutic agents in the form of charged ions. Ionizable therapeutic agents, eg, in the form of a salt which when dissolved forms charged agent ions, are preferred for iontophoretic delivery because the charged agent ions move by electromigration within the applied electric field. Electroosmosis, another type of electrotransport process, involves the movement of a liquid, which liquid contains a charged and/or uncharged therapeutic agent dissolved therein, through a biological membrane (e.g., skin) under the influence of an electric field. Another type of electrotransport, electroporation, involves the formation of transiently-existing pores in a living biological membrane by applying high voltage pulses thereto and delivery of a therapeutic agent therethrough. However, in any given electrotransport process, more than one of these processes may be occurring simultaneously to some extent. Accordingly, the term "electrotransport" is used herein in its broadest possible interpretation to include the electrically induced or enhanced transport of at least one agent, which may be charged, ie, in the form of ions, or uncharged, or of mixtures thereof, regardless of the specific mechanisms by which the agent is actually transported.

The term "anti-healing agent" means an agent which alone or in combination acts to prevent or diminish skin's natural healing processes thereby preventing the closure of the pathways formed by disruptions such as microslits/microcuts in the stratum corneum of the skin. Examples of suitable anti-healing agents include, but are not limited to:

(1) osmotic agents which include neutral compounds such as glucose, salts such as sodium chloride, and zwitterionic compounds such as amino acids.

The formulation (as is or reconstituted from a dry formulation) should have an osmotic pressure greater than about 2000 kPa and more preferably about 3000 kPa at 20° C. The osmotic pressure being calculated from the relationship:

$$\Pi = iMRT$$

where i is the van't Hoff factor, M is the molarity of the solute, R is the universal gas constant ($8.314 \: J \: K^{-1} \: mol^{-1}$) and T the temperature in degrees Kelvin.

For neutral compounds, i is 1 and the concentration at 2000 kPa is 0.8 M; and at about 3000 kPa it is 1.2 M.

Neutral compounds include:
(a) organic solvents such as dimethylsulfoxide.
(b) acids in the neutral state such as boric acid, and the like.
(c) ether alcohols and polymers of ethylene oxide comprising at least one alcohol group and having a molecular weight ranging from 92 to 500. Compounds in this group include ethoxydiglycol, diethylene glycol, dipropylene glycol, triethylene glycol, PEG-4, PEG-6, PEG-8 and PEG-9, and the like;
(d) aliphatic alcohols comprising two alcohol groups such as propylene glycol and butane diol, and the like;
(e) aliphatic alcohols comprising three alcohol groups such as glycerol, and 1,2,6-hexanetriol, and the like;
(f) tetrahydric alcohols such as erythritol and threitol, and the like;
(g) pentahydric alcohols such as adonitol, xylitol and arabitol, and the like;
(h) hexahydric alcohols such as sorbitol, mannitol, galactitol, and the like;
(i) aliphatic compounds comprising one ketonic or aldehyde group and at least two alcohol groups. Compounds in this group include deoxyribose, ribulose, xylulose, psicose, sorbose, and the like.
(j) cyclic polyols such as inositol, and the like;
(k) monosaccharides such as apiose, arabinose, lyxose, ribose, xylose, digitoxose, fucose, quercitol, quinovose, rhamnose, allose, altrose, fructose, galactose, glucose, gulose, hamamelose, idose, mannose, tagatose, and the like;
(l) disaccharides such as sucrose, trehalose, primeverose, vicianose, rutinose, scillabiose, cellobiose, gentiobiose, lactose, lactulose, maltose, melibiose, sophorose, and turanose, and the like.

For salts with i=2, the concentration of the salt at about 2000 kPa is about 0.4 M; at about 3000 kPa it is about 0.6 M. These salts include: sodium chloride, the salt forms of acetic acid, propionic acid, glycolic acid, pyruvic acid, hydracrylic acid, lactic acid, pivalic acid, beta-hydroxybutyric acid, glyceric acid, sorbic acid, mandelic acid, atrolactic acid, tropic acid, quinic acid, glucuronic acid, gluconic acid, gulonic acid, glucoheptonic acid, benzilic acid, ammonia, monoethanolamine, diethanolamine, aminomethylpropanediol, tromethamine, triethanolamine, galactosamine and glucosamine.

For salts with i=3, the concentration of the salt at about 2000 kPa is about 0.3 M; at about 3000 kPa it is about 0.4 M. These salts include: the salt forms of phosphoric acid, malonic acid, fumaric acid, maleic acid, succinic acid, tartronic acid, oxaloacetic acid, malic acid, alpha-ketoglutaric acid, citramalic acid, and tartaric acid.

For salts with i=4, the concentration of the salt at about 2000 kPa is about 0.2 M; at about 3000 kPa it is about 0.3 M. These salts include: the salt forms of aconitic acid, citric acid and isocitric acid.

For zwitterionic compounds, i is about 1 and the concentration at about 2000 kPa is about 0.8 M; at about 3000 kPa it is about 1.2 M.

Zwitterionic coumpounds include: amino acids such as glycine, alanine, proline, threonine and valine, diamino acids such as glycylglycine, buffers such as 4-morpholinepropane sulfonic acid (MOPS), (2-{[tris(hydroxymethyl) methyl] amino}-1-ethane sulfonic acid (TES),4-(2-hydroxyethyl)-1-piperazineethane sulfonic acid (HEPES), β-hydroxy-4-(2-hydroxyethyl)-1-piperazinepropane sulfonic acid monohydrate (HEPPSO), tricine, bicine, CHES and CAPS and the like.

(2) Anticoagulants such as citric acid, citrate salts (e.g. sodium citrate), dextran sulfate sodium, EDTA, pentosan polysulfate, oligonucleotides, aspirin, low molecular weight heparin, and lyapolate sodium.

(3) anti-inflammatory agents such as betamethasone 21-phosphate disodium salt, triamcinolone acetonide 21-disodium phosphate, hydrocortamate hydrochloride, hydrocortisone 21-phosphate disodium salt, methylprednisolone 21-phosphate disodium salt, methylprednisolone 21-succinate sodium salt, paramethasone disodium phosphate, prednisolone 21-succinate sodium salt, prednisolone 21-m-sulfobenzoate sodium salt, prednisolone 21-diethylaminoacetate hydrochloride, prednisolone sodium phosphate, prednylidene 21-diethylaminoacetate hydrochloride, triamcinolone acetonide 21-disodium phosphate; the salt form of NSAIDs such as aspirin and other salicylates, bromfenac, diclofenac, diflunisal, etodolac, fenoprofen, ibuprofen, indomethacin, ketoprofen, ketorolac, meclofenamate, mefenamic acid, naproxen, oxaprozin, piroxicam, sulindac, tolmetin; and antiinflammatory peptides such as antiflammin 1 and antiflammin 2; and (4) agents that effect cellular migration such as laminin and related peptides and fibronectin related peptides.

The range of concentration for anticoagulant agents, anti-inflammatory agents, and agents that inhibit cellular migration is between 0.1 and 10% in the formulation.

MODES FOR CARRYING OUT THE INVENTION

The major barrier properties of the skin, such as resistance to diffusion of drugs, reside with the outermost layer of the skin, i.e., the stratum corneum. The inner division, i.e., the backing layers, of the epidermis generally comprises three layers commonly identified as stratum granulosum, stratum malpighii, and stratum germinativum. There is essentially little or no resistance to transport or to absorption of an agent through these layers. Therefore, in order to enhance transdermal flux, the microprotrusions used to create pathways in the body surface in accordance with the present invention need only penetrate through the stratum corneum in order for the agent to be transdermally delivered or sampled with little or no resistance through the skin.

There have been many attempts to mechanically penetrate or disrupt the skin thereby creating pathways into the skin in order to enhance the transdermal flux.

However, the pathways created by the microslits/microcuts are quickly closed and sealed by the skin's natural healing processes. Accordingly, the enhancement in transdermal agent flux provided by these pathways is completely eliminated within several hours of making the pathways. The present invention inhibits the decrease in the transdermal flux of an agent due to the pathway closure after the pathways have been made.

In one of its embodiments, the skin is treated with a microprotusion array device to form small cuts, slits, or holes called pathways in the outermost layer of the body surface to a limited depth. The microprotrusions may be formed in different shapes, such as needles, hollow needles, pins, punches, and combinations thereof. An agent delivery or sampling reservoir is placed in contact with the pretreated region of the body surface to deliver or sample the agent. The agent delivery or sampling reservoir contains an anti-healing agent(s) which is co-delivered with the agent. This anti-healing agent prevents or at least inhibits the pathways from closing and hence inhibits the decrease in the transdermal flux of the agent to be delivered or sampled. Alternatively, the anti-healing agent reservoir and the agent delivery or sampling reservoir may be different reservoirs.

Figure 8:
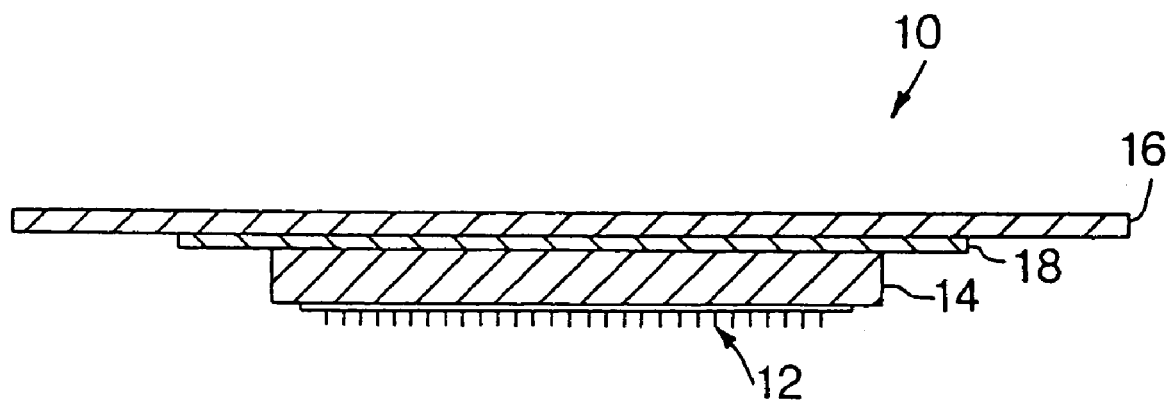
FIG. 8 is a schematic side view of a device for transdermally delivering or sampling an agent according to the present invention.

FIG. 8 illustrates a transdermal delivery or sampling patch 10 including a plurality of microprotrusions 12, a reservoir 14, an adhesive backing layer 16, and an impermeable backing layer 18. Although the reservoir 14 has been illustrated on a skin distal side of the microprotrusions 12, it should be understood that the reservoir may also be located in other positions. For example, a reservoir 14 may be provided by a discreet layer on the skin proximal or skin distal side of the base sheet which supports the microprotrusions 12. The reservoir 14 may be provided by coatings on the microprotrusions, and/or the reservoir may be provided by coatings on the other parts of the patch 10. Although the present invention has been described as including an agent and an anti-healing agent, it should be understood that the agent and the anti-healing agent may be provided in the same reservoir or different reservoirs in the device.

The device of the present invention can be used in connection with agent delivery, agent sampling, or both. In particular, the device of the present invention is used in connection with transdermal drug delivery, transdermal analyte sampling, or both. Transdermal delivery devices for use with the present invention include, but are not limited to, passive devices, electrotransport devices, osmotic devices, and pressure-driven devices. Transdermal sampling devices for use with the present invention include, but are not limited to, passive devices, reverse electrotransport devices, negative pressure driven devices, and osmotic devices. The transdermal devices of the present invention may be used in combination with other methods of increasing agent flux, such as skin permeation enhancers.

EXAMPLES

The following preparations and examples are given to enable those skilled in the art to more clearly understand and practice the present invention. They should not be considered as limiting the scope of the invention but merely as being illustrative and representative thereof.

Example 1

Decrease in drug flux has been studied with three model drugs presenting different charge characteristics: pentosan polysulfate (PPS), a highly negatively charged compound, DECAD, a synthetic model decapeptide bearing two positive charges at pH 5.5, and inulin, a neutral polysaccharide. These compounds do not penetrate the skin significantly without the use of penetration enhancers or physical disruption of the skin barrier.

In this experiment, PPS, DECAD, and inulin were delivered by passive diffusion through pathways in the skin created by pretreatment with a microprotrusion array. Pretreatment involves placing a microprotrusion array onto the skin with sufficient force to create a plurality of microslits/microcuts through the stratum corneum of the skin. The microprotrusion array is then removed from the skin and then some form of agent delivery device or agent reservoir is placed over the pathways in order to effect agent delivery or sampling. Pretreatment was used instead of integrated system because pathway closure appears to occur more rapidly and more reproducibly following pretreatment than when the microprotrusions are left in the skin during drug delivery. The concentration of PPS was below the concentration required for anticoagulant effect. All drugs were dissolved in water and solutions were gelled with 2% hydroxyethylcellulose. Concentration of PPS, DECAD and inulin were 0.1 mg/mL, 13 mg/mL and 2.5 mg/mL, respectively. PPS and DECAD were radiolabeled with tritium. Inulin was radiolabeled with $^{14}C$.

In hairless guinea pigs (HGPs), the skin of one flank was manually stretched bilaterally at the time of application of the system. Microprotrusion array application was performed with an impact applicator. The system applied comprised a foam double adhesive ring (diameter 3.8 cm, thickness 0.16 cm) with a 2 $cm^2$ reservoir in the middle containing a microprotrusion array having an area of 2 $cm^2$ and comprised of a stainless steel sheet having a thickness of 0.025 mm, trapezoidally shaped blades bent at an angle of approximately 90° to the plane of the sheet, the microprotrusions had a length of 545 micrometer, and a microprotrusion density of 72 microprotrusions/$cm^2$. Following application, the stretching tension was released. The adhesive ring was left adhered on the skin and the microprotrusion array was removed. The drug formulation (350 μL) was dispensed into the drug compartment and a backing membrane was applied to the adhesive outer surface of the ring to seal the system. A total of six HGPs were treated with the same drug formulation. At 1 hour and 24 hours after application, the systems from 3 HGPs from each group were removed and residual drug washed from the skin. The amount of drug that had penetrated during these time intervals was determined by measuring urinary excretion of radioactivity for two days following removal of the patch and corrected from the percentage excreted following iv injection (previous studies had shown that for $^3$H-PPS, $^3$H DECAD, and $^{14}$C inulin, percentage excreted over two days following injection were 32%, 65% and 94%, respectively). The results (Table I) show that between 1 hour and 24 hour, flux decreased by at least one order of magnitude for all drugs indicating that pathways formed by piercing of the skin by the microprotrusions had at least partially closed.

TABLE I

Flux of model drugs following Microprotrusion array pretreatment

| | Drug Flux (µg/(cm²h)) | |
|---|---|---|
| | 1 h | 24 h |
| PPS 0.05 mg/mL | 0.177 ± 0.039 | 0.015 ± 0.002 |
| DECAD 12 mg/mL | 1.77 ± 0.39 | 0.097 ± 0.035 |
| Inulin 2.5 mg/mL | 13.9 ± 1.6 | 0.489 ± 0.123 |

Example 2

Inhibition of pathway collapse by chemical agents was studied following pretreatment of the skin with a microprotrusion array and application of a formulation containing the agent for 24 h. Quantitation was performed by evaluation of dye impregnation of the pathways.

In HGPs, the skin of one flank was manually stretched bilaterally at the time of application. Application of the microprotrusion array was performed with an impact applicator. The system applied comprised a foam double adhesive ring (diameter 3.8 cm, thickness 0.16 cm) with a 2 cm² reservoir in the middle containing a microprotrusion array having an area of 2 cm² and comprised of a stainless steel sheet having a thickness of 0.025 mm, trapezoidally shaped blades bent at an angle of approximately 90° to the plane of the sheet. The microprotrusions had a length of 545 micrometer, and a microprotrusion density of 72 microprotrusions/cm². Following application, the stretching tension was released. The adhesive ring was left adhered on the skin and the microprotrusion array was removed. A formulation (350 µL) containing the tested compound in water and optionally a gelling agent (hydroxyethylcellulose (HEC) at 2% or silica gel at 50%) was dispensed into the drug reservoir and a backing membrane was applied to the adhesive outer surface of the ring to seal the system. The guinea pig received a second system containing a different formulation on the opposite site. Twenty four hours after application, three systems from each group were removed and residual formulation washed from the skin. The skin was stained with a 1% methylene blue solution. Excess dye was thoroughly removed with 70% isopropyl alcohol pads and a picture of the site was taken. Pictures were scored on a 0 to 5 scale, 5 being the dye uptake obtained immediately following microprotrusion array application and 0 being the dye uptake obtained after 24 h contact with a control formulation. A score of 0.5 or greater was considered significant. Various osmotic agents, anticoagulants, antiinflammatory agents, gelling agents as well as gels of different pH and various additives were tested (Table II). Among the osmotic agents, the most effective agents were the polyol 1,2,6-hexanetriol, glucuronic acid, the polymer of ethylene oxide diethylene glycol, the pentahydric alcohol adonitol, the hexahydric alcohol sorbitol, the polyol-amine tromethamine, and the monosaccharide glucose. Among the anticoagulants, citric acid, EDTA, as-well as dextran 5000 were the most effective agents in preventing pathway closure. The antiinflammatory agents betamethasone disodium phosphate as well as ketoprofen sodium salt presented a significant effect. The keratolytic agent salicylic acid also had an effect on pathway closure. Low pH also inhibited pathway closure. Surfactants (anionic, cationic and nonionic), at non-irritating concentrations, had no effect. Inert agents failed to prevent pathway closure. Sites exposed to glycerol and citric acid were also stained with India ink to confirm that the pathways were open for larger sized compounds.

TABLE II

Inhibition of Pathway Closure by Chemicals as evaluated with methylene blue following Microprotrusion array Pretreatment

| Additive class | Additive | Concentration | Score |
|---|---|---|---|
| Osmotic agents | Dimethylsulfoxide | 10% (1.3 M) | 1.0 ± 0.0 |
| | Ethanol | 0% (4.3 M) | 0 ± 0 |
| | Isopropyl alcohol | 30% (5 M) | 0.2 ± 0.2 |
| | Propylene glycol | 70% (9.2 M) | 1.0 ± 0.6 |
| | | 50% (6.6 M) | 1.3 ± 0.1 |
| | | 30% (3.9 M) | 0.7 ± 0.2 |
| | 1-3 Butane diol | 50% (5.5 M) | 0.2 ± 0.2 |
| | 2-3 Butane diol | 50% (5.5 M) | 2.2 ± 0.2 |
| | 1-2 Butane diol | 50% (5.5 M) | 2.0 ± 0.8 |
| | 1-4 Butane diol | 50% (5.5 M) | 3.0 ± 0.3 |
| | Diethylene glycol | 50% (4.7 M) | 3.2 ± 0.2 |
| | Thiodiglycol | 50% (4.1 M) | 0.3 ± 0.3 |
| | Ethoxydiglycol | 50% (3.7 M) | 0.5 ± 0.3 |
| | Triethylene glycol | 50% (3.3 M) | 3.7 ± 0.3 |
| | | 30% (2 M) | 3.3 ± 0.3 |
| | | 10% (0.7) | 1.3 ± 0.3 |
| | PEG-4 | 50% (2.6 M) | 2 ± 0.6 |
| | PEG-12 | 50% (0.9 M) | 0 ± 0 |
| | PEG-350 | 50% (0.03 M) | 0 ± 0 |
| | Glycerin | 70% (7.6 M) | 2.7 ± 0.3 |
| | | 50% (5.4 M) | 3.0 ± 0.2 |
| | | 30% (3.3 M) | 2.7 ± 0.2 |
| | 1,2,6-Hexanetriol | 50% (3.7 M) | 3.8 ± 0.2 |
| | | 23% (1.7 M) | 3.0 ± 0.5 |
| | | 11% (0.8 M) | 2.0 ± 0.3 |
| | Inositol | 10% (0.6 M) | 1.5 ± 0.3 |
| | Erythritol | 30% (2.5 M) | 3.3 ± 0.4 |
| | Adonitol | 50% (3.3 M) | 3.7 ± 0.3 |
| | | 23% (1.5 M) | 3.5 ± 0.3 |
| | | 11% (0.7 M) | 3.0 ± 0.3 |
| | Sorbitol | 50% (2.7 M) | 3.3 ± 0.3 |
| | | 23% (1.3 M) | 3.3 ± 0.3 |
| | | 11% (0.6 M) | 1.3 ± 0.6 |
| | Ribose | 50% (3.3 M) | 2.3 ± 0.3 |
| | D-Glucose | 50% (2.8 M) | 4.0 ± 0.3 |
| | | 23% (1.3 M) | 3.5 ± 0.5 |
| | | 11% (0.6 M) | 1.8 ± 0.6 |
| | | 5% (0.3 M) | 1.5 ± 0.0 |
| | L-Glucose | 23% (1.3 M) | 3.5 ± 0.3 |
| | Sucrose | 50% (1.5 M) | 1.7 ± 0.6 |
| | Trehalose | 50% (1.5 M) | 1.5 ± 0.0 |
| | NaCl | 3.5% (0.6 M) | 1.8 ± 0.2 |
| | Sodium acetate | 4.9% (0.6 M) | 1.7 ± 0.1 |
| | Ammonium acetate | 4.9% (0.6 M) | 2.1 ± 0.1 |
| | Glycolic acid, sodium salt | 24% (2.4 M) | 2.7 ± 0.1 |
| | | 12% (1.2 M) | 2.6 ± 0.1 |
| | | 6% (0.6 M) | 1.7 ± 0.1 |
| | Gluconic acid sodium salt | 30% (1.4 M) | 4.5 ± 0.0 |
| | | 13% (0.6 M) | 3.3 ± 0.0 |
| | | 10% (0.5 M) | 2.7 ± 0.2 |
| | Glucuronic acid sodium salt | 13% (0.6 M) | 3.0 ± 0.3 |
| | | 10% (0.5 M) | 3.5 ± 0.3 |
| | | 5% (0.2 M) | 1.0 ± 0.0 |
| | Ammonium chloride | 3.2% (0.6 M) | 2.6 ± 0.1 |
| | Tromethamine | 50% (3.2 M) | 3.7 ± 0.3 |
| | hydrochloride | 9.5% (0.6 M) | 2.3 ± 0.3 |
| | Galactosamine hydrochloride | 50% (2.3 M) | 2.8 ± 0.3 |
| | Malic acid, disodium salt | 11% (0.6 M) | 2.1 ± 0.3 |
| | Tartaric acid, disodium salt | 12% (0.6 M) | 1.5 ± 0.4 |
| | Glycine | 9% (1.2 M) | 1.8 ± 0.3 |
| Surfactants | Sodium dodecyl sulfate | 0.01% | 0 ± 0 |
| | Cetyl pyridinium | 0.01% | 0 ± 0 |

TABLE II-continued

Inhibition of Pathway Closure by Chemicals as evaluated with methylene blue following Microprotrusion array Pretreatment

| Additive class | Additive | Concentration | Score |
|---|---|---|---|
| | chloride | | |
| | Tween20 | 1% | 0.2 ± 0.2 |
| Inert agents | Fumed silica (Cab.O.Sil[7]) | 14% | 0 ± 0 |
| | Silica gel (2-25 ?m) | 50% | 0 ± 0 |
| | Hydroxyethyl-cellulose | 3% | 0 ± 0 |
| | | 2% | 0 ± 0 |
| | | 0.75% | 0 ± 0 |
| pH | 4.5 | 0.15 M acetate buffer | 0.8 ± 0.4 |
| | 7 | 0.15 M MOPS buffer | 0 ± 0 |
| | 9 | 0.15 M Boric acid buffer | 0.3 ± 0.2 |
| Anticoagulants | EDTA | 5% | 1.3 ± 0.2 |
| | Citric acid disodium salt | 3% | 1.2 ± 0.2 |
| | | 1% | 0.3 ± 0.2 |
| | | 0.5% | 0 ± 0 |
| | Dextran 5000 | 5% | 2.2 ± 0.4 |
| | Oligonucleotide (ISIS 2302) | 5% | 0.7 ± 0.2 |
| | Pentosan polysulfate | 5% | 0.5 ± 0.0 |
| | | 0.01% | 0 ± 0 |
| | Heparin | 2% | 0.3 ± 0.2 |
| Antiinflammatory agents | Betamethasone phospate Na | 2% | 2.3 ± 0.4 |
| | Ketoprofen Na | 2% | 2.3 ± 0.6 |
| Calcium supplement | Calcium chloride | 2% | 0.7 ± 0.4 |
| Actin polymerization inhibitor | Cytochalasin D | 0.025% | 1.5 ± 0.0 |
| Laminin and related peptides | Laminin | 0.05% | 1.0 ± 0.3 |
| | Ser-Ile-Lys-Val-Ala-Val | 0.05% | 0.5 ± 0.5 |
| | Tyr-Ile-Gly-Ser-Arg-NH$_2$ | 0.05% | 0.3 ± 0.3 |
| Fibronectin related peptides | Arg-Gly-Asp | 1% | 0.7 ± 0.4 |
| Miscellaneous | Insulin | 3 mM | 0.2 ± 0.2 |

Example 3

Pentosan polysulfate (PPS), a highly negatively charged compound, does not penetrate the skin significantly without the use of penetration enhancers or physical disruption of the skin barrier. In this experiment, PPS was delivered by passive diffusion through pathways in the skin created by a microprotrusion array. The concentration of PPS was below the concentration required for inhibition of pathway collapse (see Table II). Therefore, at the concentration used in this experiment, PPS behaved like a drug lacking any activity on pathway closure. The purpose of the experiment was to show that inhibitors of pathway collapse identified in Example 2 also improved drug flux through the skin in vivo.

Figure 2:
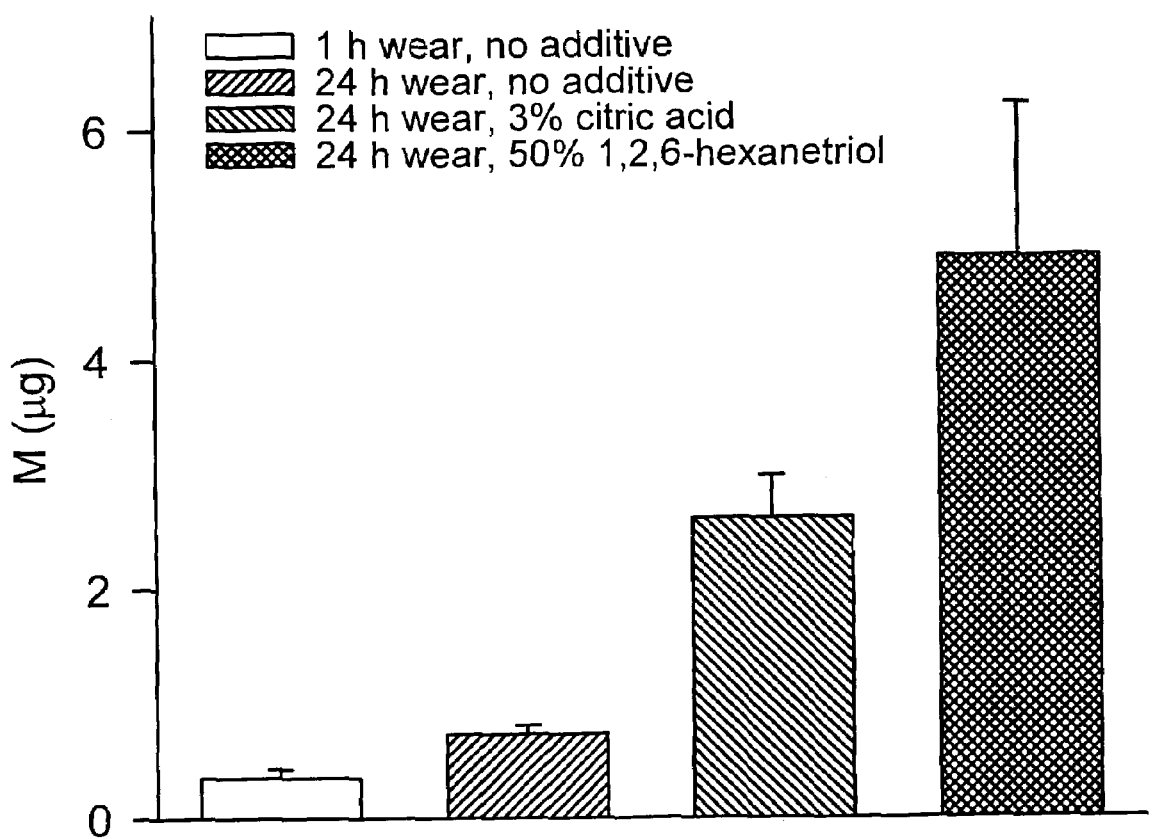
FIG. 2 is a graph of the effect of pathway closure inhibitors on passive transdermal pentosan polysulfate delivery.

In all guinea pigs, the skin of one flank was manually stretched bilaterally at the time of the application of the system. Microprotrusion array application was performed with an impact applicator. The system applied comprised a foam double adhesive ring (diameter 3.8 cm, thickness 0.16 cm) with a drug containing hydrogel having a skin contact area of 2 cm$^2$ in the middle containing a microprotrusion array having an area of 2 cm$^2$ and comprised of a stainless steel sheet having a thickness of 0.025 mm, trapezoidally shaped blades bent at an angle of approximately 90° to the plane of the sheet, the microprotrusion had a length of 545 μm, and a microprotrusion density of 72 microprotrusion/cm$^2$. Following application, the stretching tension was released. The adhesive ring was left adhered on the skin and the microprotrusion array was removed. A hydrogel containing $^3$H-PPS in water (PPS concentration of 0.1 mg/mL, 2% HEC, 350 μL) was dispensed into the drug compartment and a plastic cover was applied to the adhesive outer surface of the ring to seal the system. Additional groups of HGPs were treated in the same way, except that the formulation contained 3% citric acid trisodium salt or 50% 1,2,6-hexanetriol. At 1 and 24 h after application, 3 systems from each group were removed and residual drug washed from the skin. The amount of drug penetrated during these time intervals was determined by measuring urinary excretion of tritium (previous studies had shown that in HGPs, 32% of the tritium derived from $^3$H-PPS injected intravenously is excreted in urine). The results, as shown in FIG. 1, show that between 1 hour and 24 hours, flux decreased by about 12 fold, demonstrating pathway closure. Citric acid and 1,2,6-hexanetriol inhibited this decrease in flux. Flux in the presence of 1,2,6-hexanetriol was decreased by less than 2 fold between 1 and 24 h. Total amount transported was increased about 4 and 7 folds in the presence of citric acid and 1,2,6-hexanetriol, respectively, as compared to controls as shown in FIG. 2.

Example 4

Figure 3:
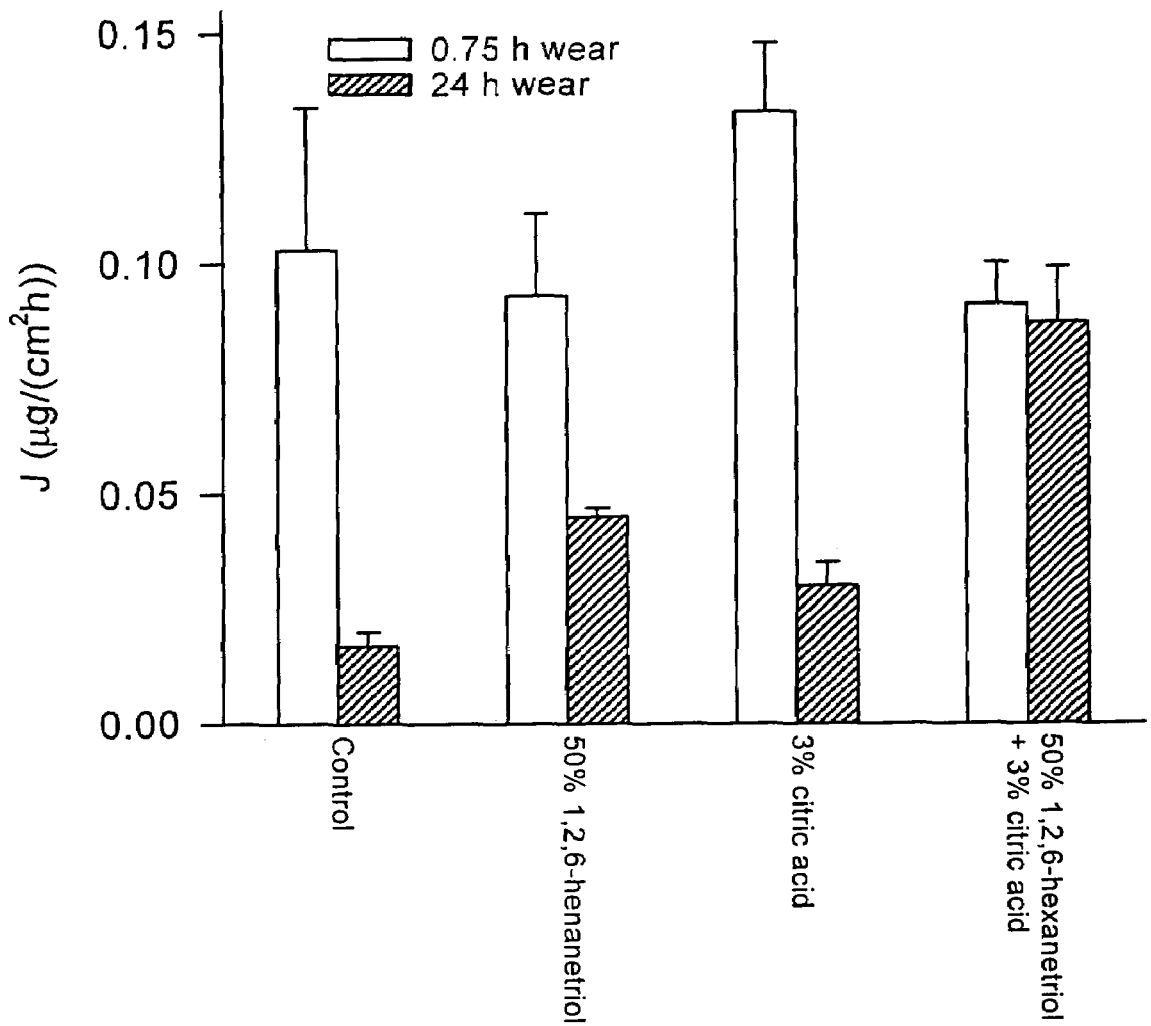
FIG. 3 is a graph of the effect of pathway closure inhibitors on passive transdermal pentosan polysulfate flux.
Figure 4:
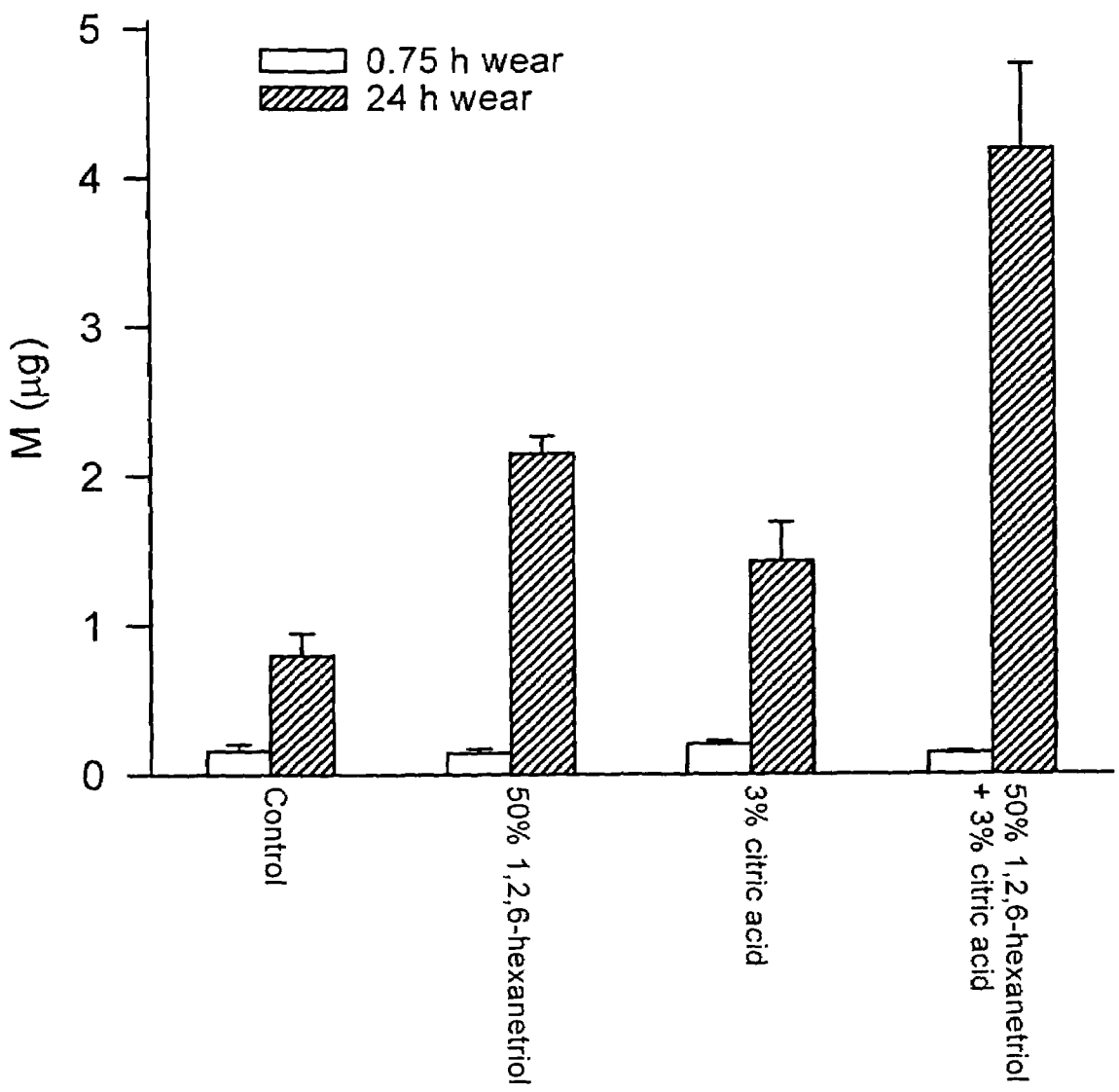
FIG. 4 is a graph of the effect of pathway closure inhibitors on passive transdermal pentosan polysulfate delivery.

A second experiment was performed with PPS. Conditions were identical to that described in Example 3 except that the microprotrusion array had shorter blades, length 194 micrometer, and higher microprotrusion density (190 microprotrusion/cm$^2$). PPS concentration was 0.16 mg/mL and was still below the concentration required for inhibition of pathway collapse. Evaluation was performed at 45 min instead of 1 h. In addition, additional groups of animals received a formulation containing the mixture of 3% citric acid trisodium salt and 50% 1,2,6-hexanetriol. Similarly to the precedent example, results shown in FIG. 3 show that between 0.75 and 24 h, flux decreased dramatically, demonstrating pathways shutdown. The additive used did not modify the 45 min PPS flux, indication that they did not present permeation enhancing properties and that pathways had not significantly closed during this period. At 24 hours, citric acid and 1,2,6-hexanetriol inhibited significantly the decrease in flux. Flux in the presence of the mixture of citric acid trisodium salt and 1,2,6-hexanetriol resulted in a complete inhibition of the decrease in PPS flux observed between 45 min and 24 h. Total amounts of PPS transported are shown in FIG. 4. The effect observed in the presence of 3% citric acid trisodium salt and 50% 1,2, 6-hexanetriol is greater than additive. This is probably the indication that these two agents are effective on different wound healing mechanisms (citric acid is probably preventing clot formation while 1,2,6-hexanetriol is probably preventing another regeneration process such as keratinocyte migration).

Example 5

Figure 5:
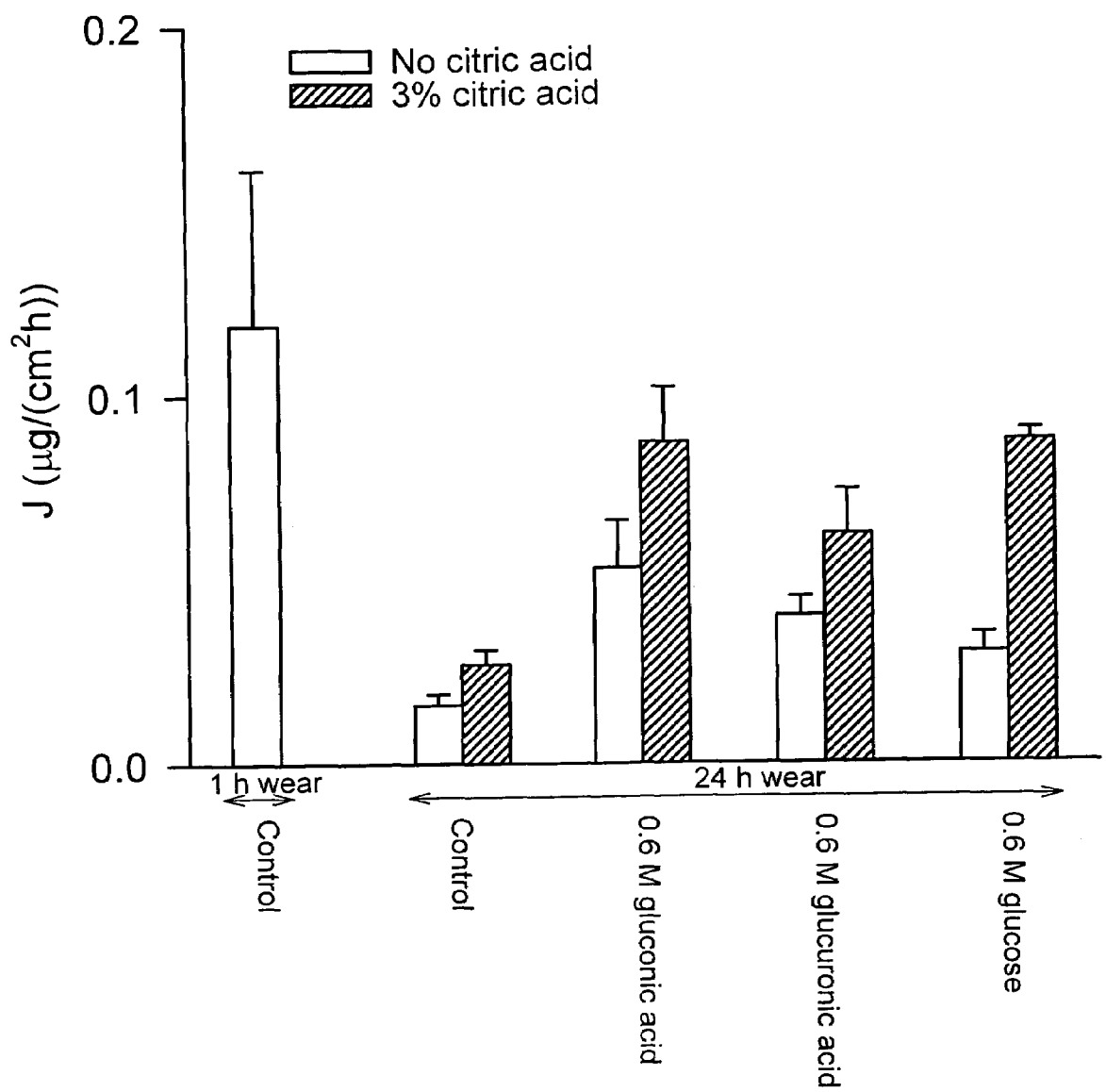
FIG. 5 is a graph of the effect of pathway closure inhibitors on passive transdermal pentosan polysulfate delivery.
Figure 6:
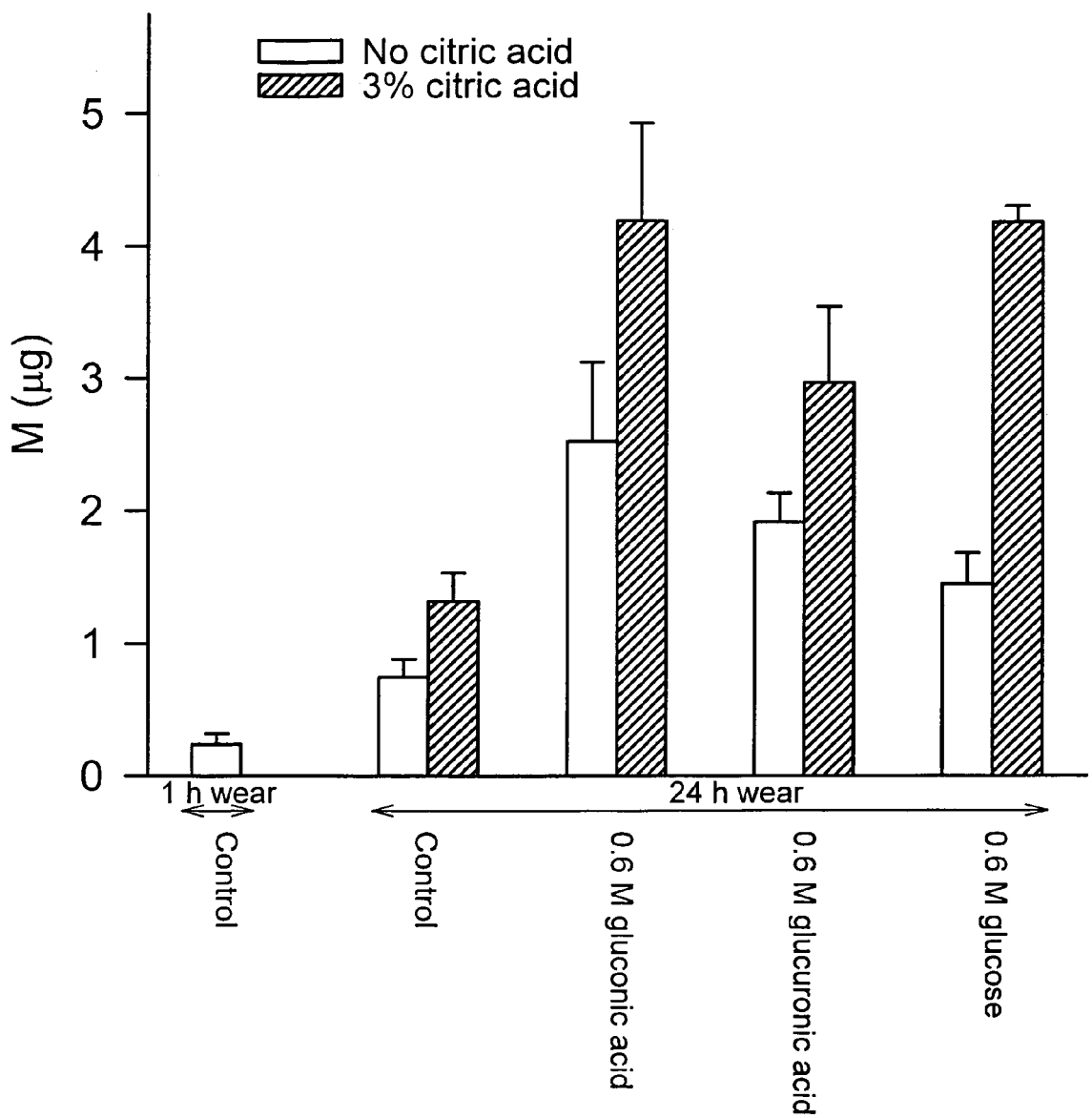
FIG. 6 is a graph of the effect of pathway closure inhibitors on passive transdermal pentosan polysulfate delivery.
Figure 7:
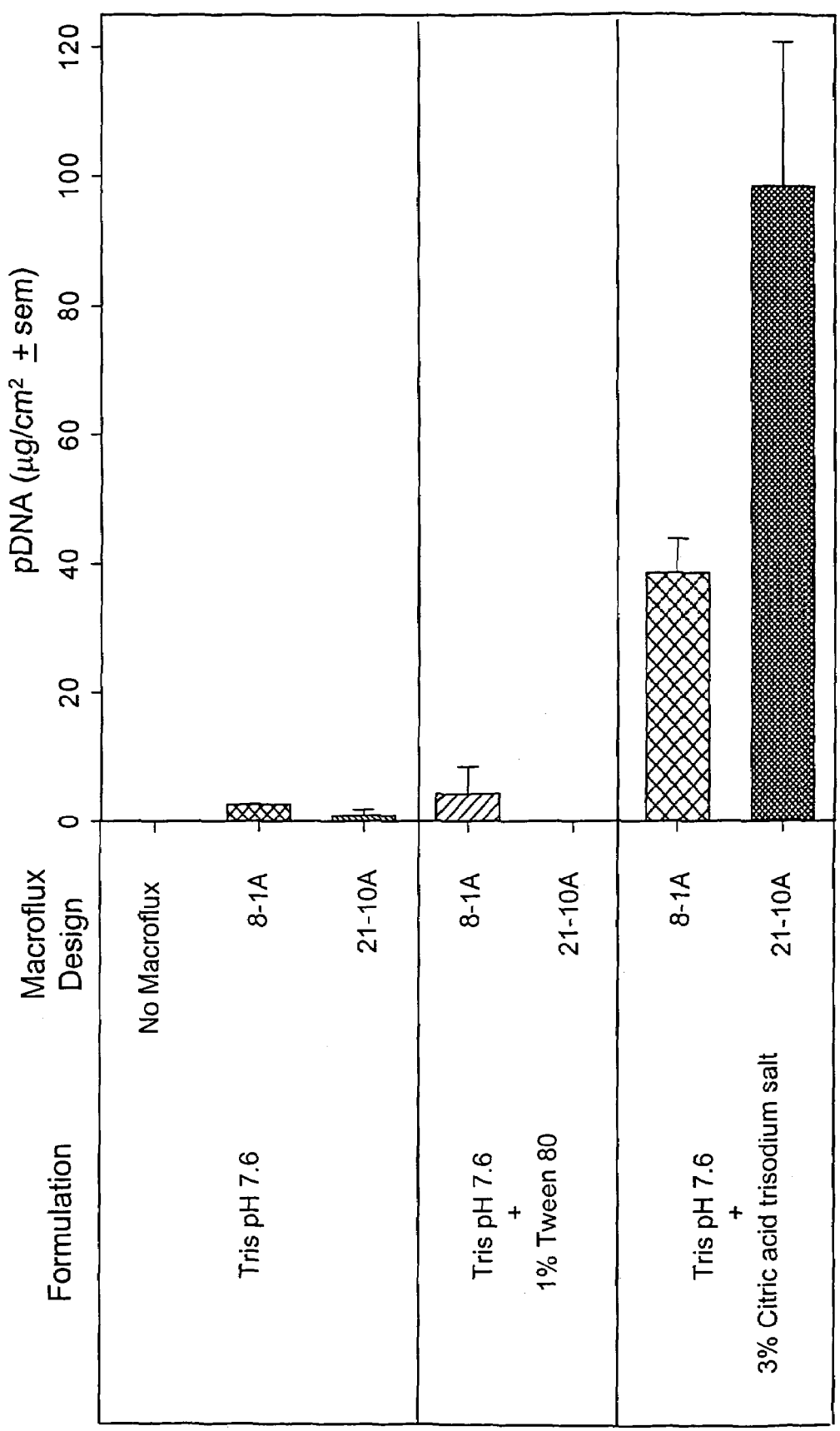
FIG. 7 is a graph of the effect of pathway closure inhibitors on passive transdermal DNA delivery.

An additional experiment was performed with PPS. Conditions were identical to that described in Example 4. Gluconic acid sodium salt, glucuronic acid sodium salt and glucose were evaluated at 0.6 M concentration with or without 3% citric acid. Similarly to the precedent example, as shown in FIG. 5, results show that between 1 hour and 24 hours, flux decreased dramatically, demonstrating pathways closure. At 24 hours, all compounds and combinations significantly increased PPS flux. Total amounts of PPS transported are shown in FIG. 6. These results support the conclusions presented in Example 4 and demonstrate that lower concentrations of anti-healing agents are still very effective at inhibiting microprotrusion pathway closure.

Example 6

Feasibility studies were conducted in hairless guinea pigs (HGPs) to determine whether passive intracutaneous delivery of a plasmid DNA vaccine (pCMV-AYW-HBs-Mkan), which encodes for hepatitis B surface antigen [HBsAg]), could be achieved using Macroflux. In all guinea pigs, the skin of one flank was manually stretched bilateraly at the time of the application of the system. Application of the microprotrusion array was performed with an impact applicator. The system applied comprised a foam double adhesive ring (diameter 2.5 cm, thickness 0.08 cm) with a 1 $cm^2$ reservoir in the middle.

One of two configurations of microprotrusion arrays were used. Specifications of the two arrays are given in the table below. Each configuration has a total surface area of 2 $cm^2$ and an active total blade surface area of 1 $cm^2$.

| Type | microprotrusions length | protrusions/$cm^2$ |
|---|---|---|
| 8-1A | 545 μm | 72 |
| 21-10A2 | 430 μm | 190 |

A microprotrusion array of the selected type was adhered to the adhesive foam and covered the bottom of the reservoir (after application, the microprotrusion array is in contact with the skin). Following application, the stretching tension was released and the microprotrusion array was left in situ. A liquid formulation (90 μL) containing 3.5 mg/mL of the plasmid DNA vaccine in buffer (TRIS 5 mM pH 7.6) was dispensed into the drug reservoir and a backing membrane was applied to the adhesive outer surface of the ring to seal the system. Additional HGPs were treated in the same way, except that the formulation contained either 1% Tween 80 or 3% citric acid trisodium salt in addition to the plasmid DNA and the Tris buffer. At 1 hour after application, two systems from each group were removed and residual formulation washed from the skin. The amount of drug penetrated at that time was determined in a 6 mm diameter full thickness skin biopsy taken at the skin site. The biopsy was dissolved in a digestion buffer (sodium dodecyl sulfate/proteinase K) and relevant DNA content was evaluated by polymerase chain (PCR) reaction followed by electrophoresis of the PCR product. A positive control group was included which consisted of 10 μg plasmid DNA injected intradermally. Negative controls consisted of the plasmid DNA applied on the skin without the use of a microprotrusion array. The results demonstrated that plasmid DNA can be successfully delivered using microprotrusion array devices under passive delivery (FIG. 7). No plasmid DNA could be detected in skin when the plasmid DNA was applied without use of the microprotrusion array (negative controls). Comparison between groups showed that the most efficient formulation contained citric acid trisodium salt. At one hour, a more than 10 fold increase in plasmid DNA delivered was observed in the presence of citric acid trisodium salt as compared to the control formulation. There was no significant enhancement of plasmid DNA delivered in the formulations containing Tween 80. With citric acid, use of the 21-10A microprotrusion array resulted in an increase in the amount of plasmid DNA delivered, of 2.5 fold as compared to the 8-1A microprotrusion array, which is consistent with greater number of protrusions in the 21-10A array.

Example 7

Examples 2-6 demonstrate that drugs of interest can have their flux enhanced by co-delivery of pathway closure inhibitors. In particular, it was shown that compounds presenting anticoagulants properties are effective in preventing pathway collapse. If these compounds can prevent pathway collapse and therefore prolong the delivery of drug molecules, it is obvious that if they are delivered at concentrations high enough to exert locally their anticoagulant activity, they will prolong their own delivery. Delivery experiments with drugs presenting anticoagulant properties have been performed in the HGP with PPS and the phosphorothiolated oligonucleotide ISIS 2302. PPS is a drug used in the management of inflammatory conditions such as interstitial cystitis, and the phosphorothiolated oligonucleotide ISIS 2302 is an antisense drug to the mRNA coding for the ICAM1 molecule and presenting antiinflammatory properties. Both molecules are highly negatively charged compound and do not penetrate the skin significantly without the use of penetration enhancers or physical disruption of the skin barrier.

With PPS at a concentration of 300 mg/mL, a total dose of 6.5±1.1 mg was delivered in 24 hours in the HGP from a 2 $cm^2$ passive pretreatment system identical to that described in Example 3 (application was performed manually, using a microprotrusion array having an area of 2 $cm^2$ and comprised of a stainless steel sheet having a thickness if 0.025 mm, trapezoidally shaped blades bent at an angle of approximately 90° to the plane of the sheet, the microprotrusion had a length of 430 μm, and a microprotrusion density of 190 microprotrusions/$cm^2$). The dose excreted in urine (2 mg) was found to be more than 85% intact. This contrasts with oral administration of PPS where a 300 mg daily dose presents a bioavailability of 1 to 3% (3 to 9 mg absorbed). In addition, following oral delivery, less than 5% of the dose absorbed was found intact in urine, indicating that transdermal administration of PPS using the microprotrusion array effectively bypasses the liver.

Additional experiments were performed with PPS in order to test alternative modes of delivery. With PPS at a concentration of 50 mg/mL, a total dose of 1.9 ±0.1 mg was delivered in 4 hours by electrotransport with a current of 100 μA/$cm^2$ and a microprotrusion array having an area of 2 $cm^2$ and comprised of a stainless steel sheet having a thickness of 0.025 mm, trapezoidally shaped blades bent at an angle of approximately 90° to the plane of the sheet, the microprotrusions had a length of 480 μm, and a microprotrusion density of 241 microprotrusion/$cm^2$. By comparison, with the same microprotrusion array and the same PPS concentration, total dose from a transdermal microprotrusion array with integrated drug reservoir and a pretreatment with a microprotrusion array and subsequent application of a drug reservoir was 2.2±0.2 mg and 1.4±0.2 mg, respectively. Collectively, these results demonstrate that PPS can be effectively delivered through the skin for extended periods of time probably as a result of its anticoagulant properties.

The phosphorothiolated oligonucleotide ISIS 2302 was delivered for 24 hours using a microprotrusion array with an area of 2 $cm^2$, microprotrusion lengths of 480 μm and 241 microprotrusions/$cm^2$. The effect of drug concentration, microprotrusion array pretreatment versus integrated treatment and delivery passive versus electrotransport were evaluated. Results, summarized in Table III, demonstrate that this compound can be effectively delivered through the skin for extended periods of time, probably as a result of its anticoagulant properties.

TABLE III

Transdermal Delivery of ISIS 2302

| Drug conc. (mg/mL) | Total dose delivered (mg) | | | |
|---|---|---|---|---|
| | Microprotrusion Pretreatment | | Integrated Treatment | |
| | Passive | Electro-transport | Passive | Electro-transport |
| 5 | 0.17 ± 0.02 | 0.47 ± 0.05 | 0.20 ± 0.04 | 0.35 ± 0.05 |
| 50 | 2.6 ± 0.7 | 6.4 ± 0.5 | 7.4 ± 1.5 | 8.3 ± 1.4 |
| 200 | 10.0 ± 1.9 | 15.6 ± 3.8 | 14.0 ± 3.2 | 15.2 ± 1.8 |

Drugs of interest that could be delivered at therapeutic levels using the microprotrusion technology during extended periods of time (i.e. 24 hours) and without the help of adjuvant that prevent pathway collapse include all compounds presenting anticoagulants properties during local delivery and having a molecular weight greater than about 2000. These compounds include pentosan polysulfate, oligonucleotides, low molecular weight heparin, hirudin and hirudin analogs such as hirulog. It will be appreciated by those of ordinary skill in the art that the invention can be embodied in other specific forms without departing from the spirit or essential character thereof. The presently disclosed embodiments are therefore considered in all respects to be illustrative and not restrictive. The scope of the invention as indicated by the appended claims rather than the foregoing description, and all changes which come within the meaning and range of equivalence thereof are intended to be embraced therein.

What is claimed is:

1. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first therapeutic agent under substantially identical conditions except in the absence of said at least one anti-healing agent; wherein said anti-healing agent is provided in an amount sufficient to achieve a flux decrease of less than a 2-fold between 1 and 24 hours.

2. A mechanical device for causing transdermal flux of a therapeutic agent comprising: a patch comprising one or more stratum corneum piercing microprotrusion which are capable of forming microslits in at least the stratum corneum of the skin in order to form pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first therapeutic agent under substantially identical conditions except in the absence of said at least one anti-healing agent; wherein said anti-healing agent is provided in an amount sufficient to achieve a flux decrease of less than a 2-fold between 1 and 24 hours.

3. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first therapeutic agent under substantially identical conditions except in the absence of said at least one anti-healing agent, and wherein the anti-healing agent is selected from the group consisting of anticoagulants, anti-inflammatory agents, agents that inhibit cellular migration, and osmotic agents and mixtures thereof; wherein said anti-healing agent is provided in an amount sufficient to achieve a flux decrease of less than a 2-fold between 1 and 24 hours.

4. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first agent under substantially identical conditions except in the absence of said at least one anti-healing agent, said anti-healing agent is selected from the group consisting of anticoagulants, anti-inflammatory agents, agents that inhibit cellular migration, and osmotic agents and mixtures thereof and wherein said anticoagulant is selected from the group consisting of heparin having a molecular weight from 3000 to 12,000 daltons, pentosan polysulfate, citric acid, citrate salts, EDTA, and dextrans having molecular weight from 2000 to 10,000 daltons, aspirin and lyapolate sodium; wherein said anti-healing agent is provided in an amount sufficient to achieve a flux decrease of less than a 2-fold between 1 and 24 hours.

5. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first therapeutic agent under substantially identical conditions except in the absence of said at least one anti-healing agent, wherein the anti-healing agent is selected from the group consisting of anticoagulants, anti-inflammatory agents, agents that inhibit cellular migration, and osmotic agents and mixtures thereof; and wherein said anti-inflammatory agent is selected from the group consisting of hydrocortisone sodium phosphate, betamethasone sodium phosphate, and triamcinolone sodium phosphate; wherein said anti-healing agent is provided in an amount sufficient to achieve a flux decrease of less than a 2-fold between 1 and 24 hours.

6. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first therapeutic agent under substantially identical conditions except in the absence of said at least one anti-healing agent, wherein the anti-healing agent is selected from the group consisting of anticoagulants, anti-inflammatory agents, agents that inhibit cellular migration, and osmotic agents and mixtures thereof; and wherein the agent that inhibits cellular migration is laminin; wherein said anti-healing agent is provided in an amount sufficient to achieve a flux decrease of less than a 2-fold between 1 and 24 hours.

7. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first therapeutic agent under substantially identical conditions except in the absence of said at least one anti-healing agent, wherein the anti-healing agent is selected from the group consisting of anticoagulants, anti-inflammatory agents, agents that inhibit cellular migration, and osmotic agents and mixtures thereof; and wherein said osmotic agent is a biologically compatible salt of an osmotic agent;-wherein said anti-healing agent is provided in an amount sufficient to achieve a flux decrease of less than a 2-fold between 1 and 24 hours.

8. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first therapeutic agent under substantially identical conditions except in the absence of said at least one anti-healing agent, wherein said anti-healing agent is selected from the group consisting of anticoagulants, anti-inflammatory agents, agents that inhibit cellular migration, and osmotic agents and mixtures thereof; and wherein said osmotic agent, in solution, generates an osmotic pressure greater than about 2,000 kilopascals at 20° C.; wherein said anti-healing agent is provided in an amount sufficient to achieve a flux decrease of less than a 2-fold between 1 and 24 hours.

9. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first therapeutic agent under substantially identical conditions except in the absence of said at least one anti-healing agent; and wherein the first therapeutic agent is a therapeutic agent and said device delivers said therapeutic agent transdermally into the skin;-wherein said anti-healing agent is provided in an amount sufficient to achieve a flux decrease of less than a 2-fold between 1 and 24 hours.

10. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first agent under substantially identical conditions except in the absence of said at least one anti-healing agent; and wherein the first agent is a therapeutic agent and said device delivers said therapeutic agent transdermally into the skin, and wherein the agent comprises a macromolecular agent;-wherein said anti-healing agent is provided in an amount sufficient to achieve a flux decrease of less than a 2-fold between 1 and 24 hours.

11. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first agent under substantially identical conditions except in the absence of said at least one anti-healing agent; and wherein the first agent is a therapeutic agent and said device delivers said therapeutic agent transdermally into the skin, and wherein the macromolecular agent is selected from the group consisting of polypeptides, proteins, oligonucleotides, nucleic acids and polysaccharides; wherein said anti-healing agent is provided in an amount sufficient to achieve a flux decrease of less than a 2-fold between 1 and 24 hours.

12. A mechanical device for causing transdermal flux of an agent comprising: a patch comprising a microprotrusion array comprising one or more stratum corneum-piercing microprotrusions which are capable of disrupting the skin by the formation of microslits in the stratum corneum of the skin in order to form pathways therethrough; and at least one reservoir comprising a first agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first agent under substantially identical conditions except in the absence of said at least one anti-healing agent; and wherein the first agent is a therapeutic agent and said device delivers said therapeutic agent transdermally into the skin; wherein said anti-healing agent is provided in an amount sufficient to achieve a flux decrease of less than a 2-fold between 1 and 24 hours.

13. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first agent under substantially identical conditions except in the absence of said at least one anti-healing agent; and wherein the first therapeutic agent is a body analyte that is transdermally sampled; wherein said anti-healing agent is provided in an amount sufficient to achieve a flux decrease of less than a 2-fold between 1 and 24 hours.

14. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first therapeutic agent under substantially identical conditions except in the absence of said at least one anti-healing agent; and wherein the first agent is the body analyte glucose that is transdermally sampled; wherein said anti-healing agent is provided in an amount sufficient to achieve a flux decrease of less than a 2-fold between 1 and 24 hours.

15. A mechanical device for causing transdermal flux of a therapeutic agent comprising: a patch comprising a microprotrusion array comprising one or more stratum corneum-piercing microprotrusions which are capable of disrupting the skin by the formation of one or more microslits in the stratum corneum of the skin which form one or more pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first therapeutic agent under substantially identical conditions except in the absence of said at least one anti-healing agent; and wherein the first therapeutic agent is a body analyte that is transdermally sampled;-wherein said anti-healing agent is provided in an amount sufficient to achieve a flux decrease of less than a 2-fold between 1 and 24 hours.

16. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in Therapeutic agent transdermal flux when compared to the transdermal flux of said first therapeutic agent under substantially identical conditions except in the absence of said at least one anti-healing agent; and wherein the anti-healing agent is delivered: (a) before any transdermal flux of the first agent; (b) before and during transdermal flux of the first agent; (c) during transdermal flux of the first agent; or (d) during and after transdermal flux of the first agent; wherein said anti-healing agent is provided in an amount sufficient to achieve a flux decrease of less than a 2-fold between 1 and 24 hours.

17. A mechanical device for causing A transdermal flux of a therapeutic agent comprising: a patch comprising one or more stratum corneum piercing microprotrusion which are capable of forming microslits in at least the stratum corneum of the skin in order to form pathways therethrough; said microprotrusion having a length of less than 0.5 mm; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first agent under substantially identical conditions except in the absence of said at least one anti-healing agent; wherein said anti-healing agent is provided in an amount sufficient to achieve a flux decrease of less than a 2-fold between 1 and 24 hours.

18. A mechanical device for causing transdermal flux of a therapeutic agent comprising: a patch comprising one or more stratum corneum-piercing microprotrusions which are capable of disrupting the skin by the formation of one or more microslits in the stratum corneum of the skin which form one or more pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first therapeutic agent under substantially identical conditions except in the absence of said at least one anti-healing agent; and wherein the first agent is a body analyte that is transdermally sampled; and wherein the microprotrusions and the reservoir are an integral element; wherein said anti-healing agent is provided in an amount sufficient to achieve a flux decrease of less than a 2-fold between 1 and 24 hours.

19. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first therapeutic agent under substantially identical conditions except in the absence of said at least one anti-healing agent; and wherein the first therapeutic agent is selected from the group consisting of heparin having a molecular weight from 3000 to 12,000 daltons, pentosan polysulfate, citric acid, citrate salts, EDTA, and dextrans having molecular weight from 2000 to 10,000 daltons; wherein said anti-healing agent is provided in an amount sufficient to achieve a flux decrease of less than a 2-fold between 1 and 24 hours.

20. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first therapeutic agent and at least one anti-healing agent which are different from each other, said at least one reservoir is capable of being placed in agent transmitting relationship with the skin and said pathways, wherein the therapeutic agent and said at least one anti-healing agent which are different from each other are dry-coated on said one or more microprotrusions; and wherein the amount of said at least one anti-healing agent is effective in inhibiting a decrease in therapeutic agent transdermal flux when compared to the transdermal flux of said first therapeutic agent under substantially identical conditions except in the absence of said at least one anti-healing agent; wherein said anti-healing agent is provided in an amount sufficient to achieve a flux decrease of less than a 2-fold between 1 and 24 hours.

21. A mechanical device for causing transdermal flux of a therapeutic agent comprising: a patch comprising a microprotrusion array capable of forming disruptions in at least the stratum corneum of the skin in order to form pathways therethrough; and at least one reservoir comprising a first therapeutic agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first therapeutic agent under substantially identical conditions except in the absence of said at least one anti-healing agent, and wherein the anti-healing agent is selected from the group consisting of anticoagulants, antiinflammatory agents, agents that inhibit cellular migration, and neutral osmotic agents and mixtures thereof; wherein said anti-healing agent is provided in an amount sufficient to achieve a flux decrease of less than a 2-fold between 1 and 24 hours.

22. A mechanical device for causing transdermal flux of a therapeutic agent comprising: a patch comprising one or more stratum corneum piercing microprotrusion which are capable of forming microslits in at least the stratum corneum of the skin in order to form pathways therethrough; said first one reservoir comprising at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first agent under substantially identical conditions except in the absence of said at least one anti-healing agent; wherein said anti-healing agent is provided in an amount sufficient to achieve a flux decrease of less than a 2-fold between 1 and 24 hours.

23. A mechanical device for causing transdermal flux of an agent comprising: a patch comprising one or more stratum corneum piercing microprotrusion which are capable of forming microslits in at least the stratum corneum of the skin in order to form pathways therethrough, wherein the first agent is a therapeutic agent dry coated on one or more of said microprotrusions, wherein said device is capable of delivering said first agent transdermally into the skin, and at least one reservoir comprising a first agent and at least one anti-healing agent which are different from each other, said at least one reservoir is capable of being placed in agent transmitting relationship with the skin and said pathways, wherein the amount of said at least one anti-healing agent is effective in inhibiting a decrease in therapeutic agent transdermal flux when compared to the transdermal flux of said first agent under substantially identical conditions except in the absence of said at least one anti-healing agent; wherein said anti-healing agent is provided in an amount sufficient to achieve a flux decrease of less than a 2-fold between 1 and 24 hours.

24. A mechanical device for causing transdermal flux of an agent comprising: a patch comprising one or more stratum corneum piercing microprotrusion which are capable of forming microslits in at least the stratum corneum of the skin in order to form pathways therethrough, wherein the first agent is a therapeutic agent dry coated on one or more of said microprotrusions, wherein said device is capable of delivering said first agent transdermally into the skin, and at least amount of said at least one anti-healing agent is effective in inhibiting a decrease in therapeutic agent transdermal flux when compared to the transdermal flux of said first therapeutic agent under substantially identical conditions except in the absence of said at least one anti-healing agent; and wherein the first therapeutic agent and the anti-healing agent are the same compound and selected from the group consisting of heparin having a molecular weight from 3000 to 12,000 daltons, pentosan polysulfate, citric acid, citrate salts, EDTA, and dextrans having molecular weight from 2000 to 10,000 daltons; wherein said anti-healing agent is provided in an amount sufficient to achieve a flux decrease of less than a 2-fold between 1 and 24 hours.

* * * * *